(12) United States Patent
Cordes (10) Patent No.: US 9,861,312 B2
(45) Date of Patent: Jan. 9, 2018

(54) BLINDING KIT FOR CLINICAL TRIALS

(71) Applicant: Sanofi-Aventis Deutschland GmbH, Frankfurt am Main (DE)

(72) Inventor: Claus Cordes, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 369 days.

(21) Appl. No.: 14/371,788

(22) PCT Filed: Jan. 15, 2013

(86) PCT No.: PCT/EP2013/050643
§ 371 (c)(1),
(2) Date: Jul. 11, 2014

(87) PCT Pub. No.: WO2013/107725
PCT Pub. Date: Jul. 25, 2013

(65) Prior Publication Data
US 2014/0350486 A1  Nov. 27, 2014

(30) Foreign Application Priority Data

Jan. 16, 2012  (EP) ..................... 12151197

(51) Int. Cl.
*A61B 5/00* (2006.01)
*A61M 5/14* (2006.01)
(Continued)

(52) U.S. Cl.
CPC ........... *A61B 5/4848* (2013.01); *A61M 5/002* (2013.01); *A61M 5/14* (2013.01); *A61M 5/20* (2013.01);
(Continued)

(58) Field of Classification Search
CPC .. A61B 5/002; A61B 5/4848; A61M 5/31566; A61M 5/31511; A61M 5/16827;
(Continued)

(56) References Cited

U.S. PATENT DOCUMENTS 4,758,235 A * 7/1988 Tu ..................... A61M 39/223
                                                      251/311
5,411,490 A * 5/1995 Tennican ............ A61M 5/1408
                                                      600/575

(Continued)

FOREIGN PATENT DOCUMENTS

EP    1570872 A1   9/2005
WO    9705914 A1   2/1997

*Primary Examiner* — Bhisma Mehta
*Assistant Examiner* — Hamza Darb
(74) *Attorney, Agent, or Firm* — McDonnell Boehnen Hulbert & Berghoff LLP (57) ABSTRACT

The present invention relates to a blinding kit for administering a medicament to a patient in a clinical trial, the blinding kit comprising: a first blinding device having an opaque container and having an outlet for administering a liquid substance to a patient and having at least a first and a second inlet, wherein the first inlet is in permanent fluid communication with the outlet and wherein at least the second inlet is disconnected from the outlet, a second blinding device having an opaque container and having an outlet for administering a liquid substance to a patient and having at least two inlets, wherein said at least two inlets are in permanent fluid communication with the outlet.

13 Claims, 4 Drawing Sheets

(51) Int. Cl.
*A61M 5/00* (2006.01)
*A61M 5/20* (2006.01)
*A61M 5/315* (2006.01)
*A61M 5/31* (2006.01)

(52) U.S. Cl.
CPC . *A61M 5/31566* (2013.01); *A61M 2005/3125* (2013.01); *A61M 2202/0468* (2013.01)

(58) Field of Classification Search
CPC .. A61M 2005/3125; A61M 2202/0468; A61M 5/20; A61M 5/19
See application file for complete search history.

(56) References Cited

U.S. PATENT DOCUMENTS

| | | | | |
|---|---|---|---|---|
| 6,544,250 B1 * | 4/2003 | Schaffer | ............... | A61D 7/00 |
| | | | | 206/438 |
| 2008/0167621 A1 * | 7/2008 | Wagner | ............... | A61M 5/19 |
| | | | | 604/191 |

* cited by examiner

BLINDING KIT FOR CLINICAL TRIALS

CROSS REFERENCE TO RELATED APPLICATIONS

The present application is a U.S. National Phase Application pursuant to 35 U.S.C. §371 of International Application No. PCT/EP2013/050643 filed Jan. 15, 2013, which claims priority to European Patent Application No. 12151197.6 filed Jan. 16, 2012. The entire disclosure contents of these applications are herewith incorporated by reference into the present application.

FIELD OF INVENTION

The present invention relates to the field of clinical trials and in particular to a blinding kit for administering a medicament to a patient in clinical trials. The blinding kit is particularly adapted to conceal whether a medicament or an inert substance is provided and administered to the patient.

BACKGROUND

In clinical studies or trials, effectiveness of a medicament can be proved by treating a group of patients with a medicament while providing a comparative group of patients with an inert or inactive substance, like a physiological saline solution, substantially acting as a placebo.

However, depending on the type of administration of the medicament and depending on generic properties of the medicament, it may be inadmissible to administer the inert substance to the patient. If for instance a parenteral medicament features a particular colour it would be inadmissible to dye a comparative inert substance accordingly. In such cases, administration of the inert substance to the patient has to be pretended or simulated. However, neither patient nor medical staff should become aware of the pretended administration of the medicament.

Document U.S. Pat. No. 6,544,250 B1 for instance describes a device for blinding the administration of non-solid pharmaceutical presentations in clinical trials without using the so-called double-blind technique. This device is particularly designed for intrapulmonary administration of a medicament. The device comprises a blinding bag having at least two attachments. One of said attachments is intended for connection to a dispenser for the pharmaceutical presentation and the other attachment is intended for connection to an applicator.

The inside of said bag has means for holding back the pharmaceutical presentation, wherein the attachment intended for connection to the applicator has a closure inside the container. Another embodiment of said blinding bag comprises two similar attachments, wherein the attachments have a continuous connection in the inside of the container, thus ensuring that the pharmaceutical presentation is transported through the container.

However, such blinding device is not suitable for clinical trials, in which the medicament has to be administered to the patient by way of injection.

SUMMARY

It is therefore an object of the present invention to provide a blinding device and a blinding kit being universally applicable to different kinds of administration of medicaments or pharmaceutical substances. It is a further aim to increase patient safety and to improve the blinding of pharmaceutical or inert substances, both to the patient as well as to medical staff.

The present invention provides a blinding kit for administering a medicament to a patient in a clinical trial. The blinding kit comprises a first and a second blinding device, each of which having an opaque container or bag and further having an outlet for providing a liquid substance to a patient. The outlet is typically to be coupled with an injection or infusion needle, or, depending on the type of administration, to a respective applicator, that serves to transport the liquid substance to the patient.

Each of first and second blinding devices further has at least a first and a second inlet that are adapted and intended to be coupled with a supply of the liquid substance. The liquid substance to be supplied to first and second blinding devices is either a liquid medicament and/or an inert substance, like a physiological saline solution. First and second blinding devices differ in that the first inlet of the first blinding device is in permanent fluid communication or fluid connection with the outlet of the first blinding device while the other, hence, the second inlet is disconnected from said outlet. Hence, with the first blinding device, the second inlet is not in fluid communication with the outlet. The first blinding device typically comprises an absorber or a receptacle in order to collect and to store a liquid substance that is provided via the second inlet.

Moreover the second inlet is and remains permanently disconnected from the outlet. The second inlet is non-connectable to the outlet and serves as a dummy inlet. The second inlet may only serve to receive a supplied substance but is inoperable to transfer the supplied substance to the outlet.

The second blinding device is characterized in that at least two inlets are in permanent fluid communication with the outlet of the second blinding device.

First and second blinding devices comprise an almost identical outer shape and outer geometry, such that neither patient nor medical staff can distinguish between first and second blinding devices. Both, first and second inlet of first and second blinding devices are adapted to be coupled with two different supplies, providing a pharmaceutical or medicinal substance and an inert liquid substance, respectively.

Here, the first blinding device acts as a kind of placebo device since its second inlet intended to be coupled with a medicament supply is disconnected from the outlet.

With the second blinding device, both inlets are in fluid communication with the outlet. Therefore, both, the medicament as well as the inert substance will be transported through the second blinding device to its outlet and further to the patient. Hence, the second blinding device is to be used with a verum group of patient whereas the first blinding device is typically to be used with a placebo group of patients.

Irrespective on whether the first blinding device or the second blinding device is used with the placebo group or verum group, with both blinding devices of said blinding kit, a liquid substance fed via the first inlet is always transported through the blinding device to its respective outlet. Therefore, also the placebo group of patients treated with the first blinding device will at least receive a liquid but inactive substance fed via the first inlet. A risk of unblinding of the device can thus be minimized. Even when making use of the first blinding device, the patient will at least receive the inert substance provided via the first inlet. Even in the event that a patient takes notice of e.g. an injection procedure, he may not distinguish whether it is the medicament or the inert substance which is actually injected.

With both, the first and with the second blinding device, it is always intended to feed an inert substance via the first inlet and to feed a medicament via the second inlet. In case of administration of the medicament by way of injection, even patients of the placebo group may experience and notice, that they receive a liquid substance by way of injection.

Moreover, also medical staff will be substantially hindered to identify if a fluid provided to first and/or second inlet is actually urged through the outlet of the opaque container or not.

Also, by providing the first and second blinding device of the blinding kit with at least two inlets, the respective blinding device can be flushed e.g. with a physiological solution prior to administration of the liquid medicament or of the placebo. This way, even a dead volume of the blinding device itself can be filled with a physiological solution in order to avoid injection of e.g. air when administering a substance.

It is generally to be noted that first and second blinding devices are designed as self-sufficient devices. They are not interconnected with each other and are to be used alternately for the verum or placebo group of patients in a clinical trial. First and second blinding devices are also non-interconnectable to each other.

According to a preferred aspect, first and second inlets of the second blinding device are interconnected by way of a y-connector inside the container or bag. This way and downstream of first and second inlet, respective tubes merge and therefore provide a fluid communication between the outlet and both of first and second inlets. Preferably, since the first inlet is to be used to flush the dead volume of the blinding device, it is preferred, that the y-connector is disposed in close proximity to the second inlet, which is to be coupled with a supply of the liquid medicament. Moreover, by way of the first inlet, the intra-container tubes can be flushed with the inert substance even after administration of the medicament to prevent unblinding, e.g. when the device is disconnected after administration of the substance.

In a further preferred embodiment, the first blinding device comprises a collecting reservoir being in fluid communication or in fluid connection with the second inlet of the first blinding device for receiving and collecting the entirety of a substance to be fed via the second inlet. The collecting reservoir is arranged downstream of the second inlet inside the opaque container and is adapted to absorb or to accommodate a liquid substance entering the first blinding device via the second inlet.

According to another embodiment, the collecting reservoir is separately disposed inside the opaque container and comprises a hydrophilic and/or liquid absorbing substance. The collecting reservoir may for instance be filled with a water-absorbing polymer material or with a gelling agent. By arranging the collecting reservoir as a separate reservoir in the opaque container or housing of the first blinding device, the liquid substance fed via the second inlet can be confined in a pre-defined spatial region or volume defined by the collecting reservoir. This way, the substance does not spread across the entire volume of the first blinding device and/or its opaque container.

This is even of particular benefit, when the opaque container is for instance designed as a flexible but non-transparent bag. Then, first and second blinding devices may comprise a rather solid collecting reservoir disposed therein, such that neither patient nor medical staff are capable to determine a filling level of the collecting reservoir, e.g. by way of tactile sensing.

According to another preferred aspect, first and second inlets of first and/or second blinding devices comprise male and female connectors, respectively. This way, first and second inlets can be mechanically encoded in order to ensure, that an inert substance enters the blinding device via the first inlet whereas the medicament always enters the device via the second inlet. Providing first and second inlets with differently encoded connectors, inadvertent swapping or interchanging of first and second inlets can be effectively prevented.

In a further preferred embodiment, the blinding kit also comprises a first and a second delivery device to be coupled with first and second inlets of first and/or second blinding devices, respectively. Preferably, the first delivery device is to be exclusively connected and coupled with the first inlet of first and second blinding devices whereas the second delivery device is to be coupled or connected with the second inlet of the first and/or second blinding devices. Apparently, first and second delivery devices are equipped with female and male connectors in order to correspond with the connectors of first and second inlets of first and/or second blinding devices.

For example, if the first inlet of the first and/or the second blinding device comprises a male connector, the first delivery device to be interconnected with the first inlet comprises a female connector that corresponds to said male connector. First and/or second delivery devices may comprise some kind of feeding device or may be connected or coupled with some type of feeding mechanism, such like a syringe, infusor or perfusor or other medical devices adapted to administer a liquid medicament. The delivery device may comprise a syringe or cartridge, preferably being pre-filled with an inert substance or with a liquid medicament, respectively.

In a further embodiment, the first and/or second blinding device further comprises a third inlet to be coupled with a third delivery device, preferably providing an inert substance. The third inlet may either be coupled with the outlet or may end in the collecting reservoir. In embodiments of a first blinding device, representing a placebo device, the third inlet may merge with the first inlet. Respective tubes of first and third inlet therefore mutually merge and may serve for a transportation of the liquid substance to the outlet.

When the second blinding device is equipped with a third inlet, said third inlet is preferably in fluid communication with the collecting reservoir while the second inlet, adapted to receive the liquid medicament is in fluid communication with the outlet of the second blinding device. In this embodiment, the reservoir is intended to collect the inert substance, which solely for blinding purpose has to be fed to the blinding device.

Such a configuration is of particular benefit, if a patient will otherwise notice introduction or influx of a substance into e.g. dermal tissue or into his cardiovascular system. Then, in an application scenario, the first and the second inlet port may simultaneously provide a medicament and an inert substance, respectively. Depending on the type of blinding device, one of second or third inlet ports is effectively inactive due to its coupling with the collecting reservoir.

Furthermore, the first inlet either merges with the second inlet or with the third inlet, depending on which of second or third inlets is in fluid communication with the outlet. Here, the first inlet is to be coupled with a supply of an inert substance in order to flush the device prior and/or after administration of the medicament or of the placebo, respectively. By flushing the device with an inert substance even after administration of a medicament, the tubing inside the container can be flushed. Furthermore, the inert substance but not the medicament will always be present at the outlet when disconnecting said outlet from a patient. In case the medicament differs in scent or colour from the inert substance, both application scenarios, making use of either the first or the second blinding device will end up by with the inert substance being present at the outlet when device and patient are disconnected from each other.

In another embodiment, first and second blinding devices comprise a third inlet being in permanent fluid communication with the outlet. Here, first and third inlet are intended to flush the blinding device prior and after administration of the liquid substance via the second inlet, which is either coupled with the outlet or with a collecting reservoir. When the blinding kit and its first and/or second blinding devices is equipped with three inlets, the kit is preferably also provided with three different delivery devices. Inlets and corresponding devices can be mechanically or colour encoded, e.g. by way of having mutually corresponding male and female connectors, such like Luer-type connectors.

By having three inlets, handling of the blinding kit can be facilitated in that the first inlet is used for eliminating or filling of the dead volume of the blinding device to prevent administration or injection of air. The second inlet is used for administration of the medicament and/or of the inert substance and the third inlet is used for a subsequent flushing of the blinding device prior to deconnecting of blinding device and patient.

It is of further benefit when the connectors or the tube interconnected therewith comprise at least one unidirectional valve or check-valve in order to prevent backflow of the liquid substances. In particular when several tubes merge, each one of the separate tubes should be provided with such a check-valve upstream of the merging section. This way a fluid pressure present in one tube cannot propagate into the other tube which would lead to a counter-directed fluid flow.

According to a further preferred embodiment, the first and/or second blinding device is equipped with at least one protector element releasably attached to the third and/or to the second and/or to the first inlet. The protector element serves to impede access to the first and/or to the second and/or to the third inlet. By way of a single or by way of multiple protector elements, a sequence of process steps for administering the medicament can be defined.

For example, in an initial configuration, a first inlet is free to be coupled with a first delivery device. After application of a first delivery of a substance via the first inlet, a first protector element can be detached or released, e.g. from the first inlet, thereby giving way to the second inlet. Then, a similar procedure can be conducted in that a second delivery device is coupled with the second inlet in order to transport a second substance through the blinding device. Thereafter, and for the purpose of a terminal flushing of the blinding device, a second protector element can be released and/or detached in order to provide access to the third inlet.

The protector element or elements therefore provide stepwise access to first, second and third inlets and therefore demand that the blinding device is used according to a pre-defined schedule.

In still another embodiment, the at least one protector element is releasably connected to the first, to the second and/or to the third inlet by way of a protective cap covering the first, second and/or third inlet, respectively. This way, removal or releasing of the protector element first requires to remove a respective protective cap of an adjacently arranged inlet. Consequently, the protector elements are arranged in a staggered configuration at the blinding device's inlet section.

Furthermore and according to another preferred aspect, the first, second and/or third inlet and corresponding delivery devices comprise mutually corresponding labels. Additional or alternative to a mechanical encoding of delivery devices and inlets first, second and/or third inlets as well as corresponding delivery devices can be easily and unambiguously labelled and visually marked. Hence, an intuitive assignment can be provided, that serves to indicate which delivery device is to be coupled with which inlet.

It is further to be noted that the blinding kit with first and second blinding devices is by no way limited to injective administration of medicaments. It may also be generally applicable with enteral pharmaceutical forms and presentations, that are to be supplied to patients via probes or other medical devices.

BRIEF DESCRIPTION OF THE DRAWINGS

In the following, preferred embodiments of the invention will be described in detail by making reference to the drawings, in which.

DETAILED DESCRIPTION

Figure 1:
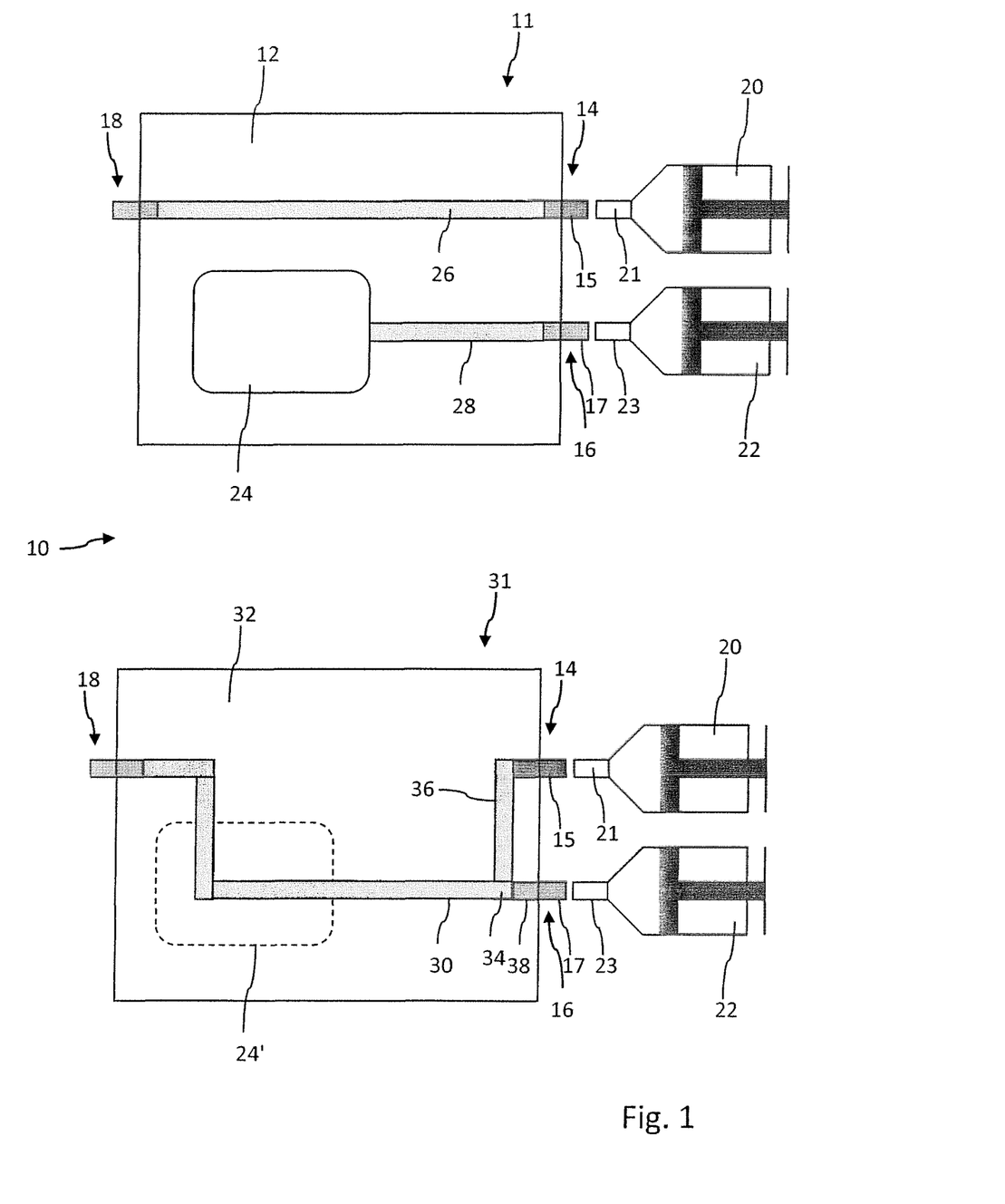
FIG. 1 illustrates a principal sketch of a first embodiment of the invention.

The blinding kit 10 as illustrated in FIG. 1 comprises a first blinding device 11 and a second blinding device 31. First and second blinding devices 11, 31 are of substantially identical outer shape and geometry. Both devices 11, 31 comprise an outlet 18 as well as two inlets 14, 16, namely a first inlet 14 and second inlet 16. Both inlets 14, 16 are to be coupled with first and second delivery devices 20, 22, that may comprise filled syringes as indicated in FIG. 1. Syringes 20, 22 comprise connectors 21, 23 that correspond with connectors 15, 17 of first and second inlets 14, 16 of first and second blinding devices 11, 31, respectively.

The blinding devices 11, 31 as shown in FIG. 1 mutually differ in that blinding device 11 is intended for usage with a placebo group of patients whereas blinding device 31 is intended to be used with a verum group of patients. For this purpose, blinding device 11 comprises a collecting reservoir 24 adapted to collect and/or to absorb a liquid substance supplied by the syringe 22 via the second inlet 16. Consequently, the second inlet 16 is connected with the collecting reservoir 24 by way of a tubing 28. In contrast to that, first inlet port 14 of the first blinding device 11 is directly connected with the outlet 18, by way of a tubing 26. Since the blinding device 11 comprises a non-transparent and opaque container or bag 12, neither patient nor medical staff will be able to find out, if the medicament provided by the syringe 22 is actually dispensed and provided to the patient via the outlet 18.

The second blinding device 31 of the blinding kit 10 according to FIG. 1 differs from the first blinding device 11 in that both inlets 14, 16 are in fluid communication with the outlet 18. For this purpose, first inlet 14 is connected with second inlet 16 by way of an y-connector 34 for merging the tubes 36, 38 in downstream direction. Each of the tubes 36, 38 is in direct fluid communication with the inlets 14, 16. By way of the y-connector 34, the tubes 36, 38 merge downstream into a tubing 30 directly leading to the outlet 18.

Even though not explicitly illustrated, the collecting reservoir 24 or the open end of the tubing 28 of the first blinding device 11 may be provided with a diffuser adapted to mimic or to provide a counter pressure which is typically perceivable when manually depressing a piston of a syringe 20, 22 being in fluid communication with biological tissue. The collecting reservoir 24 may further comprise a flexible bag filled with absorbing material. In order to inhibit unblinding of the first blinding device, the collecting reservoir 24 may alternatively comprise a rigid box. This way a user may no longer tactilely sense whether the collecting reservoir is present and/or filled with a liquid substance.

For this purpose also the second blinding device 31 may be equipped with a fake collecting reservoir 24' that has the purpose to mimic shape and geometry of a real collecting reservoir 24 of a placebo-type blinding device 11.

It is of particular benefit, when the inlets 14, 16 of first and second blinding devices 11, 31 are provided with different male or female-type connectors 15, 17, such like male or female Luer-connectors. This way, interchanging and swapping of delivery devices 20, 22, equipped with corresponding female and male connectors 21, 23 can be effectively prevented and patient safety can be enhanced respectively. Since the first delivery device 20 is always to be filled with an inert substance, such like physiological saline solution, the administration procedure is always identical, irrespective on whether a patient of the verum group or a patient of the placebo group is treated by way of a first or second blinding device 11, 31, respectively.

The various inlets 14, 16, 48 are preferably provided with unidirectional or check valves in order to prevent t backflow of the substance, especially when tubes 26, 28, 30 being in fluid communication with said inlets are mutually interconnected. The check valves or non-return valves may be positioned and arranged directly at the particular inlet 14, 16, 48 or elsewhere in the tubing 26, 28, 30 of the blinding device but preferably upstream of a y-connector 34.

Figure 2:
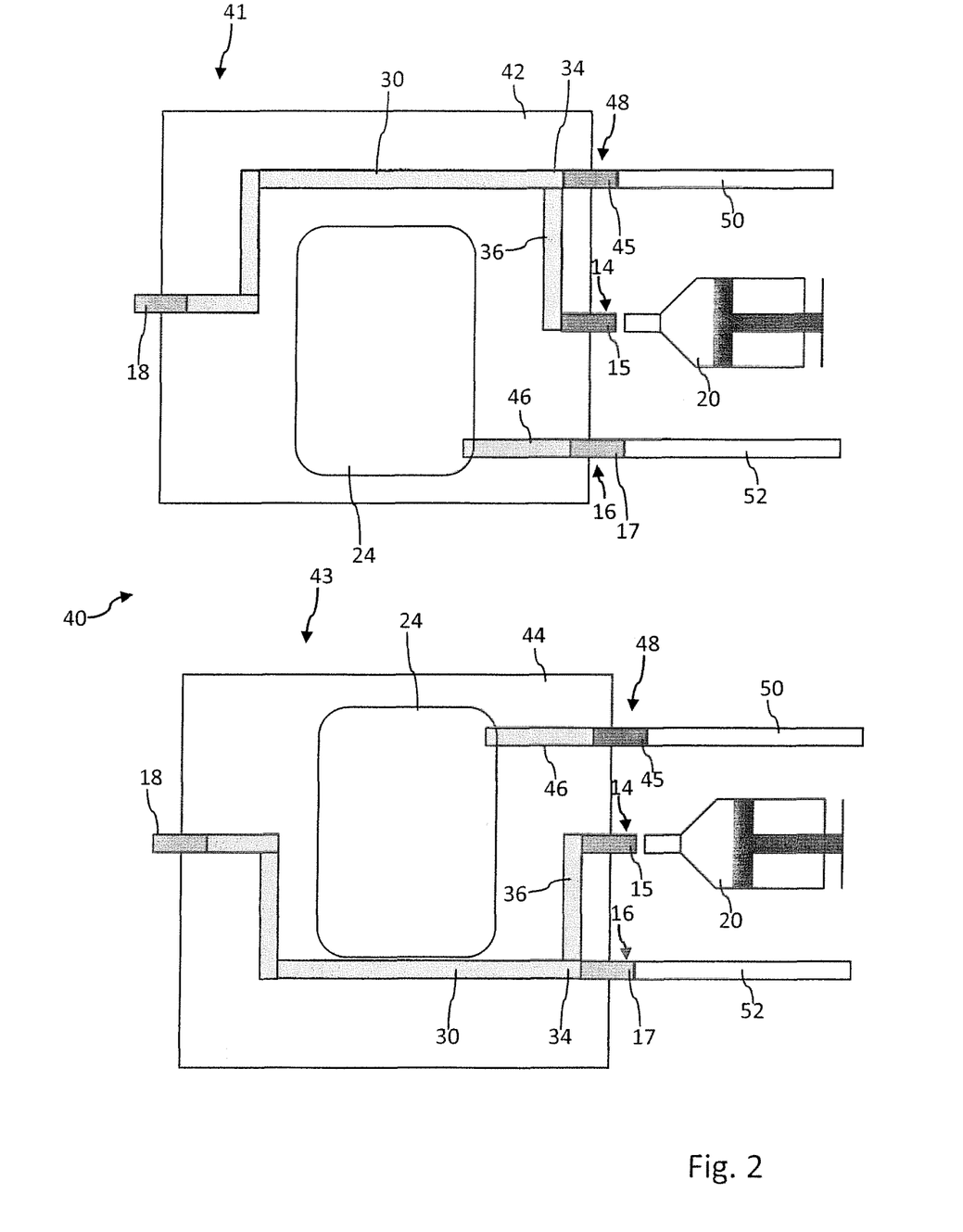
FIG. 2 schematically shows a second embodiment.

The embodiment as illustrated in FIG. 2 is particularly designed for medicaments to be administered by way of infusion. Here, a problem may arise in terms of unblinding, when the substance to be infused is generally perceptible by a patient, e.g. due to the temperature of the substance. Therefore, the embodiment according to FIG. 2 comprises a third inlet 48 having a male or female connector 45. As depicted in FIG. 2, the two blinding devices 41, 43 are to be connected with two different infusion tubes 50, 52, whereby infusion tube 50 is intended to provide an inert substance and wherein infusion tube 52 is adapted to provide a medicament. As further illustrated, the placebo-type blinding device 41 comprises a collecting reservoir 24 being in fluid communication with the second inlet 16 via a tubing 46. The residual inlets, namely first inlet 14 and third inlet 48 merge by way of an y-connector 34 and are thus in fluid communication with the outlet 18 by way of the tube 30.

Correspondingly, with the verum-type configuration of the blinding device 43, the collecting reservoir 24 is in fluid communication with the third inlet 45 via the tube 46. Then, first and second inlets 14, 16 mutually merge by means of the y-connector 34 and are in fluid communication with the outlet 18 via the tube 30. In this configuration, a medicament provided via the infusion tube 52 is directly transferred to the outlet 18, whereas the inert substance fed by the infusion tube 50 is collected by the reservoir 24.

Opaque containers 42, 44 of first and second blinding devices 41, 43 of the blinding kit 40 according to FIG. 2 are substantially identical. Moreover, if the non-transparent container 42, 44 comprises a flexible non-transparent bag, the tubes 30, 34, 36, 46 extending inside the container 42, 44 preferably extend in a similar or even identical way in order to provide and to attain a sufficient blinding of first and second blinding devices 41, 43.

With the embodiment according to FIG. 2, the patient, irrespective whether he belongs to the verum or placebo group in a clinical trial, will always receive a liquid substance, which is either an inert substance in case of blinding device 41 or a medicament, when blinding device 43 is used.

The first inlet 14 as shown with both, first and second blinding devices 41, 43 is to be used to flush the blinding device 41, 43 prior and/or after administration of the medicament or after injection of the placebo into the reservoir 24, respectively.

In case the medicament differs in colour and/or odour from the inert substance, by way of flushing the blinding device 41, 43 after administration of the medicament, an intended blinding of first and/or second blinding device 41, 43 can be easily sustained. Hence, after appropriate usage of both blinding devices, upon disconnection, it will be always the inert substance that is present at the outlet 18.

Figure 3:
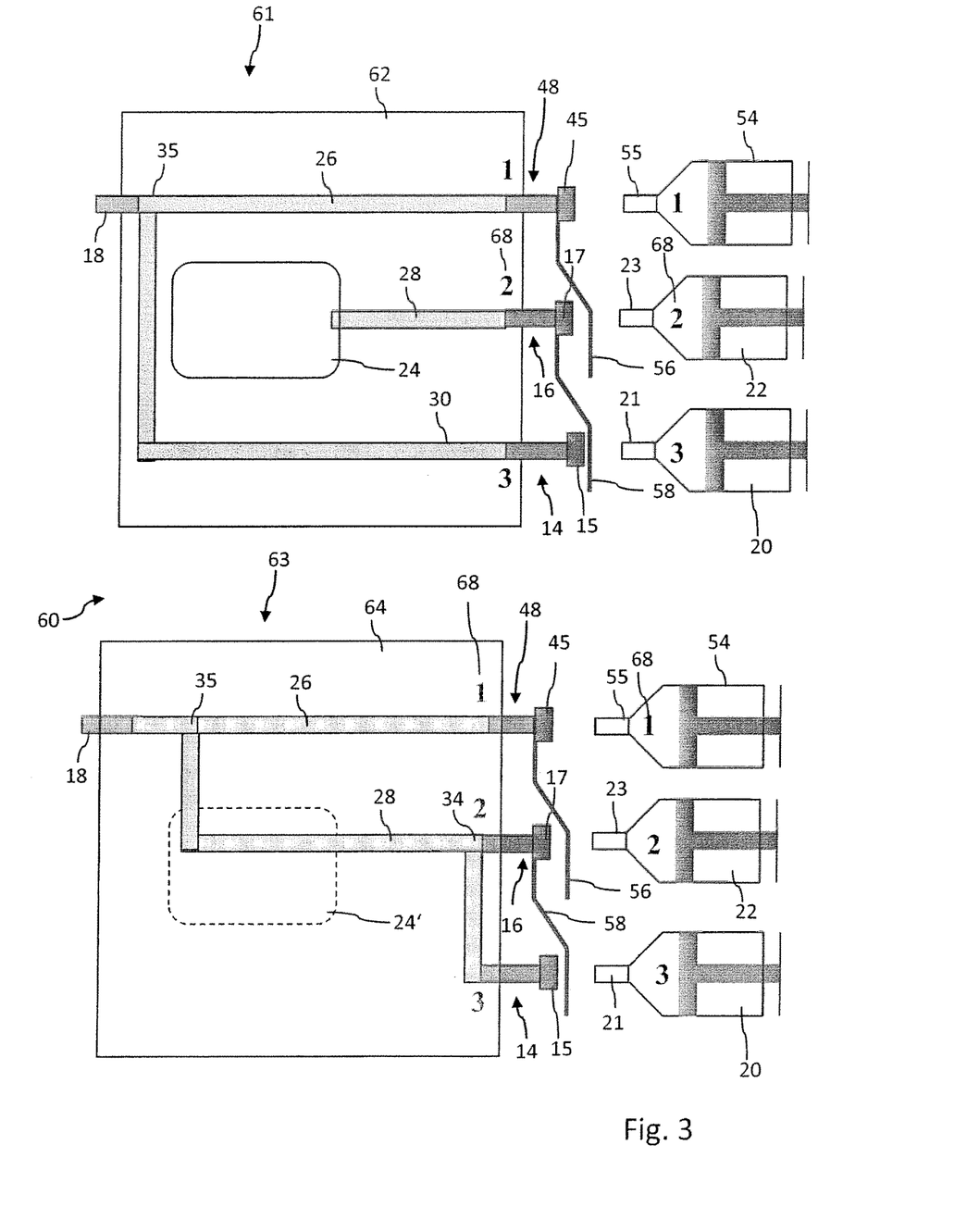
FIG. 3 is illustrative of a third embodiment of the invention.

FIG. 3 is illustrative of another embodiment of a blinding kit 60 wherein the first and second blinding devices 61, 63 feature three inlets 14, 16, 48. The blinding devices 61, 63 have opaque or non-transparent containers 62, 64, respectively. Here, the inlet ports 48, 16 and 14 are to be used in a pre-defined order. Similar to the embodiment according to FIG. 1, with both blinding devices 61, 63, the first inlet port 14 is in permanent fluid communication with the outlet 18. Similarly, also the third inlet port 48 is in permanent fluid communication with the outlet 18.

The devices 61, 63 only differ with respect to the second inlet 16. With the first blinding device 61, the second inlet 16 is in fluid communication with a collecting reservoir 24 by way of a tubing 28 in a similar way as already described with respect to FIG. 1. However, in FIG. 3, the collecting reservoir 24 is absent or is provided as a fake collecting reservoir 24' in order to conceal the inner structure of the blinding device 63 in comparison to the blinding device 61. In embodiments, wherein a fake collection reservoir 24' is implemented, the blinding device 63 mimics the geometrical contour of the blinding device 61.

The second inlet 16 of the second blinding device 63 is also in permanent fluid communication with the outlet. Hence, with the blinding device 63, all three inlets 14, 16, 48 are connected with the outlet 18 by way of two successively arranged y-connectors 34, 35.

As further illustrated in the embodiment according to FIG. 3, initial access to the first and second inlets 14, 16 is blocked by way of first and second protector elements 56, 58. By way of the protector elements 56, 58 a pre-defined schedule regarding usage of the various inlets 48, 16, 14 can be determined.

Initially, and as illustrated in FIG. 3 only a connector 45 of the third inlet 48 is accessible for a delivery device 54 having a corresponding connector 55. After using the delivery device 54, said device 54 can be disconnected from the connector 45, which in turn can be released or disconnected from the first or second blinding device 61, 63. As further indicated in FIG. 3, a third protector element 56 adapted to inhibit access to the second inlet 16 is releasably attached to the connector 45 of the third inlet 48. Upon release or removal of the protector element 56 after usage of the delivery device 54, the connector 17 of the second inlet 16 becomes accessible.

Then, the delivery device 22 can be appropriately connected with the inlet 16 and a medicament can either be dispensed to the collecting reservoir 24 of the blinding device 61 or can be transferred through the blinding device 63 and expelled via outlet 18. After dispensing of the medicament, another protector element 58 releasably attached to the connector 17 or to the inlet 16 can be released or removed, thereby giving way to the inlet 14 and its connector 15. By subsequently connecting the delivery device 20 to the inlet 14, the blinding device 61, 63 can be flushed, e.g. with an inert liquid substance in order to entirely expel a pre-defined dose of a medicament through the outlet 18 and in order to sustain blinding of the respective blinding device 61, 63.

Additionally or alternative to a mechanical encoding of various connectors 45, 55, 17, 23, 15, 21, the connectors can also be provided with a label 68 or with mutually corresponding colours. By way of a labelling, interchanging and inappropriate coupling of delivery devices 20, 22, 54 with inlet ports or connectors 15, 17, 45 can be effectively prevented. Moreover, when the label 68 comprises numbers or letters, the pre-defined schedule of coupling delivery devices and administering respective substances provided therein can be further displayed and notified to medical staff.

Figure 4:
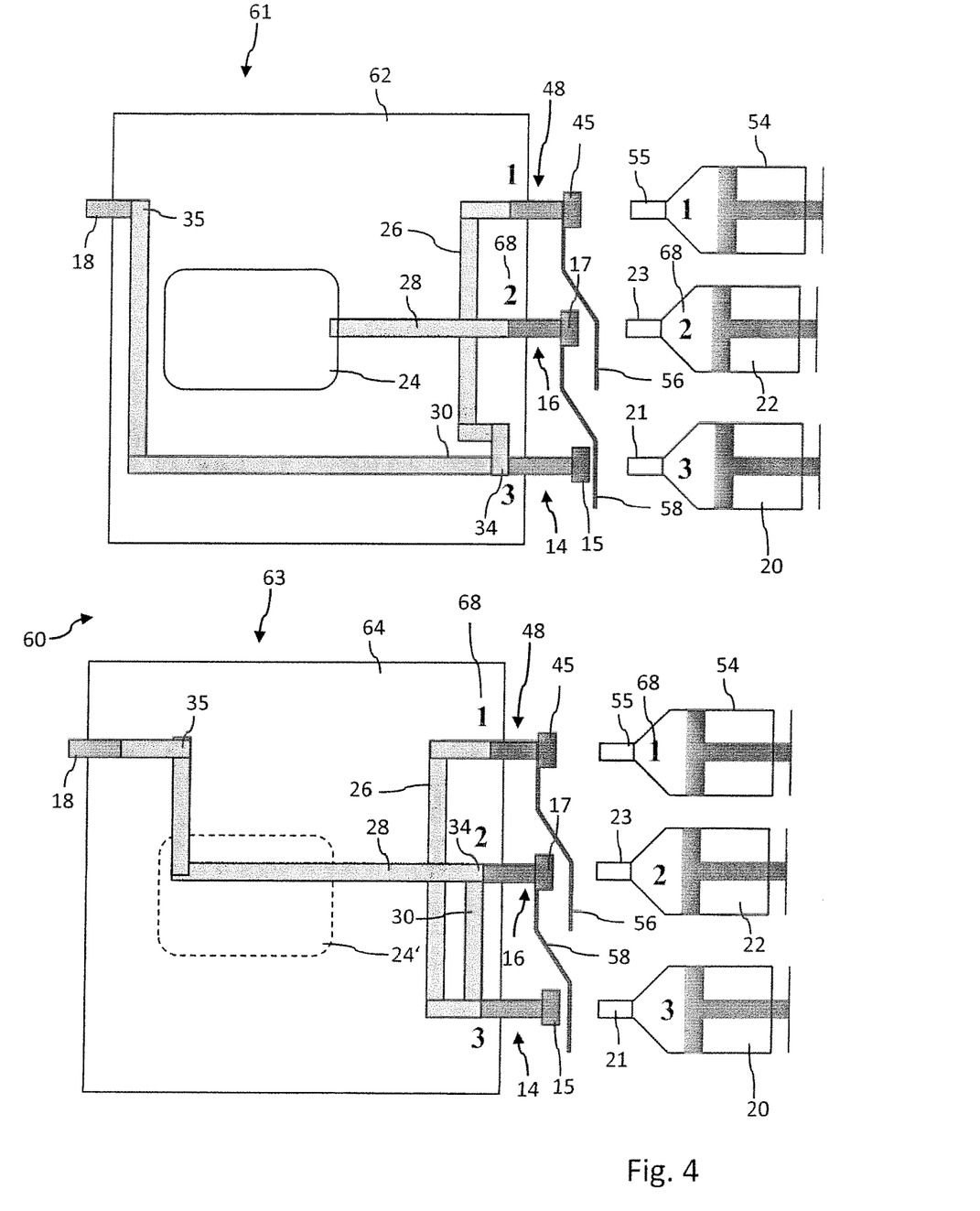
FIG. 4 shows an alternative solution of the third embodiment.

FIG. 4 is illustrative of another embodiment of the blinding kit 60, wherein the tubes 26 and 30 downstream of connectors 48 and 14 mutually merge in direct vicinity of the connectors 48, 14. Apart from that the functionality of the blinding kits 60 illustrated in FIGS. 3 and 4 is highly similar. Therefore, identical or corresponding components are denoted with the same reference numerals.

Merging of tubes 26, 30 directly downstream their respective connectors 48, 14 in embodiment according to FIG. 4 provides that a substance initially dispensed via connector 45 into the inlet 48 of the blinding device 63 sequentially flows from tube 26 into tube 30 the latter of which interconnecting inlets 14 and 16. After having passed the tube 30, the substance then flows through tube 28 also providing a fluid communication between inlet 16 and outlet 18.

Similarly, also with the blinding device 61 intended for placebo treatment, the tubes downstream of inlets 48 and 14 mutually merge in direct vicinity of respective inlets 14, 48.

With the embodiments of blinding devices 61 and 63 according to FIG. 4 it is to be noted that tubes 26 and 28 are not interconnected. With device 63, inlet 48 tube 26 is connected with tube 30 which in turn merges with tube 28 at y-connector 34. With device 61, tube 26 directly merges with tube 30 at y-connector 34 in direct vicinity of inlet 14.

In this way, an initial injection of a product through inlet 48 and tube 26 effectively serves to flush other tubes 28, 30 interconnected therewith. Then, in subsequent treatment processes, wherein at least one of the other inlets 14, 16 is flushed and provided with a liquid substance, the tubing system is already vented and injection of e.g. via the outlet 18 air can be effectively prevented.

By mutually interconnecting all inlets 48, 14, 16 in direct vicinity of their inlet connectors 45, 17, 15, an effective venting of the entire tubing system 26, 28, 30 inside the blinding device 61, 63 can be provided during an initial flush of a single inlet 48. Further injection procedures therefore do no longer require to execute a separate venting or flushing procedure. In particular, when a medicament is to be used that differs in colour and/or in scent from the inert substance the likelihood or danger of unblinding can be further reduced.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

The invention claimed is:

1. A blinding kit for administering a medicament to a patient in a clinical trial, the blinding kit comprising:
   a first blinding device having an opaque container and having an outlet for administering a liquid substance to a first patient and having at least a first and a second inlet, wherein the first inlet of the first blinding device is in permanent fluid communication with the outlet of the first blinding device, and wherein at least the second inlet of the first blinding device is disconnected from the outlet of the first blinding device; and
   a second blinding device having an opaque container and having an outlet for administering a liquid substance to a second patient and having at least a first and a second inlet, wherein the first and the second inlets of the second blinding device are in permanent fluid communication with the outlet of the second blinding device,
   wherein the first and the second blinding devices comprise an identical outer shape such that the first and the second inlets of the first blinding device and the first and the second inlets of the second blinding device are located at the same relative positions with regard to the opaque container of the first blinding device and the opaque container of the second blinding device, respectively, and
   wherein the second inlet of the first blinding device remains permanently disconnected from and is not connectable to the outlet of the first blinding device.

2. The blinding kit according to claim 1, wherein the first and second inlets of the second blinding device are interconnected by way of a y-connector inside the opaque container of the second blinding device.

3. The blinding kit according to claim 1, wherein the first blinding device comprises a collecting reservoir being in fluid connection with the second inlet of the first blinding device for receiving and collecting the entirety of a substance fed via the second inlet of the first blinding device.

4. The blinding kit according to claim 3, wherein the collecting reservoir is separately disposed inside the opaque container of the first blinding device and comprises a hydrophilic and/or liquid absorbing substance.

5. The blinding kit according to claim 1, wherein the first and the second inlet of at least one of the first and the second blinding devices comprise male and female connectors, respectively.

6. The blinding kit according to claim 1, further comprising:
   a first delivery device filled with an inert substance and being adapted to be coupled with the first inlet of the first and/or the second blinding device,
   a second delivery device filled with the medicament and being adapted to be coupled with the second inlet of the first and/or the second blinding device.

7. The blinding kit according to claim 6, wherein the first and second delivery devices comprise male and female connectors.

8. The blinding kit according to claim 1, wherein at least one of the first and/or the second blinding devices comprises a third inlet to be coupled with a third delivery device filled with an inert substance.

9. The blinding device according to claim 8, wherein the third inlet is in permanent fluid communication with the outlet of the at least one of the first and the second blinding device.

10. The blinding kit according to claim 8, wherein the first inlet and the third inlet of the first blinding device are interconnected by way of a y-connector inside the opaque container of the first blinding device.

11. The blinding kit according to claim 8, wherein access to at least one of the first inlet, the second inlet and the third inlet is blocked by at least one protector element releasably attached to at least one of the first inlet, the second inlet and the third inlet.

12. The blinding kit according to claim 11, wherein the protector element is releasably connected to at least one of the first inlet, the second inlet and the third inlet by way of a protective cap covering at least one of the first, second and third inlet.

13. The blinding device according to claim 1:
wherein the first inlet of the first blinding device comprises a first label corresponding to a label of a first delivery device filled with an inert substance,
wherein the second inlet of the first blinding device comprises a second label corresponding to a label of a second delivery device filled with the medicament, and
wherein the first blinding device comprises a third inlet to be coupled with a third delivery device filled with an inert substance, and
wherein the third inlet of the first blinding device comprises a third label corresponding to a label of the third delivery device.

* * * * *